United States Patent [19]

Metz et al.

[11] Patent Number: 5,849,307
[45] Date of Patent: Dec. 15, 1998

[54] VACCINE ADJUVANT

[75] Inventors: Christine Noël Metz, Great Neck, N.Y.; Richard J. Bucala, Cos Cob, Conn.

[73] Assignee: The Picower Institute for Medical Research, Manhasset, N.Y.

[21] Appl. No.: 827,345

[22] Filed: Mar. 26, 1997

[51] Int. Cl.⁶ .................................................. A61K 39/002
[52] U.S. Cl. ...................................... 424/278.1; 424/283.1
[58] Field of Search ................................ 424/278.1, 283.1

[56] References Cited

U.S. PATENT DOCUMENTS 4,645,670  2/1987  Zilg ............................................ 424/101
4,806,352  2/1989  Cantrell ...................................... 424/92

OTHER PUBLICATIONS

Slater et al., Proc. Acad. Natl. Sci. USA 88:325–329, 1991.

Slater, Exp. Parasitology 74:362–365, 1992.

Camus, et al., Ann. Parasitol. Hum. Comp., vol. 60, No. 5, pp. 523–532, 1985, abstract only.

*Primary Examiner*—Toni R. Scheiner
*Attorney, Agent, or Firm*—Jeffrey B. Oster

[57] ABSTRACT

There is disclosed an adjuvant composition for potentiating the immunogenicity of an antigen, comprising water or an aqueous solution and hemozoin or β-hematin.

8 Claims, 1 Drawing Sheet

VACCINE ADJUVANT

TECHNICAL FIELD OF THE INVENTION

The present invention provides novel vaccine adjuvant compositions, methods of using the vaccine adjuvant compositions and a method of using hemozoin as a vaccine adjuvant.

BACKGROUND OF THE INVENTION

Vaccine adjuvants are useful for improving an immune response obtained with any particular antigen in a vaccine composition. Adjuvants are used to increase the amount of antibody and effector T cells produced and to reduce the quantity of antigen and the frequency of injection. Although some antigens are administered in vaccines without an adjuvant, there are many antigens that lack sufficient immunogenicity to stimulate a useful immune response in the absence of an effective adjuvant. Adjuvants also improve the immune response from "self-sufficient" antigens, in that the immune response obtained may be increased or the amount of antigen administered may be reduced.

The standard adjuvant for use in laboratory animals is Freund's adjuvant. Freund's Complete adjuvant (FCA) is an emulsion containing mineral oil and killed mycobacteria in saline. Freund's incomplete adjuvant (FIA) omits the mycobacteria. Both FIA and FCA induce good humoral (antibody) immunity, and FCA additionally induces high levels of cell-mediated immunity. However, neither FCA nor FIA are acceptable for clinical use due to the side effects. In particular, mineral oil is known to cause granulomas and abscesses, and *Mycobacterium tuberculosis* is the agent responsible for tuberculosis.

There have been many substances that have been tried to be used as adjuvants, such as the lipid-A portion of gram negative bacterial endotoxin, and trehalose dimycolate of mycobacteria. The phospholipid lysolecithin exhibited adjuvant activity (Arnold et al., *Eur. J Immunol.* 9:363–366, 1979). Some synthetic surfactants exhibited adjuvant activity, including dimethyldioctadecyl ammonium bromide (DDA) and certain linear polyoxypropylenepolyoxyethylene (POP-POE) block polymers (Snippe et al., *Int. Arch. Allergy Appl. Immunol.* 65:390–398, 1981; and Hunter et al., *J. Immunol.* 127:1244–1250, 1981) While these natural or synthetic surfactants demonstrate some degree of adjuvant activity, they do not demonstrate the degree of immunopotentiation (i.e., adjuvant activity) as FCA or FIA.

Another approach has looked to break down the adjuvant effect from mycobacteria and determine adjuvant activity from a muramyl-peptide in the cell wall. The smallest fragment of this molecule that retains adjuvant activity is N-acetyl-muramyl-L-alanyl-D-isoglutamine, which is also called muramyl dipeptide (MDP) (Ellouz et al., *Biochem. & Biophys. Res. Comm.* 1317–1325, 1974). There have been many MDP derivatives prepared as vaccine adjuvants and described in U.S. Pat. Nos. 4,158,052; 4,323,559; 4,220,637; 4,323,560; 4,409,209; 4,423,038; 4,185,089; 4,406,889; 4,082,735; 4,082,736; 4,427,659; 4,461,761; 4,314,998; 4,101,536; and 4,369,178; the disclosures of each of which are incorporated by reference herein. Each of these disclosed MDP derivatives were weakly effective at stimulating the immune system when administered in aqueous solution, but the activity generally falls short of FCA or FIA.

In addition, U.S. Pat. Nos. 4,606,918; 4,770,874; and 4,772,466 (the disclosures of each of which are incorporated by reference herein) describe a glycopeptide POP-POE block polymer vaccine adjuvant in a composition containing a glycol ether-based surfactant, a metabolizable oil and buffered saline. U.S. Pat. No. 5,376,369 (the disclosure of which is incorporated by reference herein) also describes an immunopotentiating glycopeptide N,N,N',N'-tetra (polyoxypropylenepolyoxyethylene)-1,2-diaminoethane block tetra-polyol polymer also acts as an adjuvant.

The present invention was made in a continuing effort to find improved vaccine adjuvants that are readily available and have safe side effect profiles.

SUMMARY OF THE INVENTION

The present invention provides an adjuvant composition for potentiating the immunogenicity of an antigen, comprising (a) water or an aqueous solution; and (b) hemozoin or β-hematin.

Preferably, the adjuvant composition further comprises a lipid of fat emulsion comprising about 10% (by weight) vegetable oil and about 1–2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

The present invention further provides a method for inducing or enhancing the immunogenicity of an antigen in a mammal, comprising parenteral administration of a pharmaceutical composition comprising the antigen and an effective amount of hemozoin or β-hematin. Preferably, the lipid or fat emulsion comprises about 10% soybean oil and about 1.2% egg yolk phospholipids. Preferably, the antigen is selected from the group consisting of a vaccine, bacteria, virus, rickettsia, pollen, dust, danders, a poison, and venom derived from an insect or snake.

The present invention firther provides a method for using hemozoin or β-hematin as a vaccine adjuvant.

DETAILED DESCRIPTION OF THE INVENTION

Figure 1:
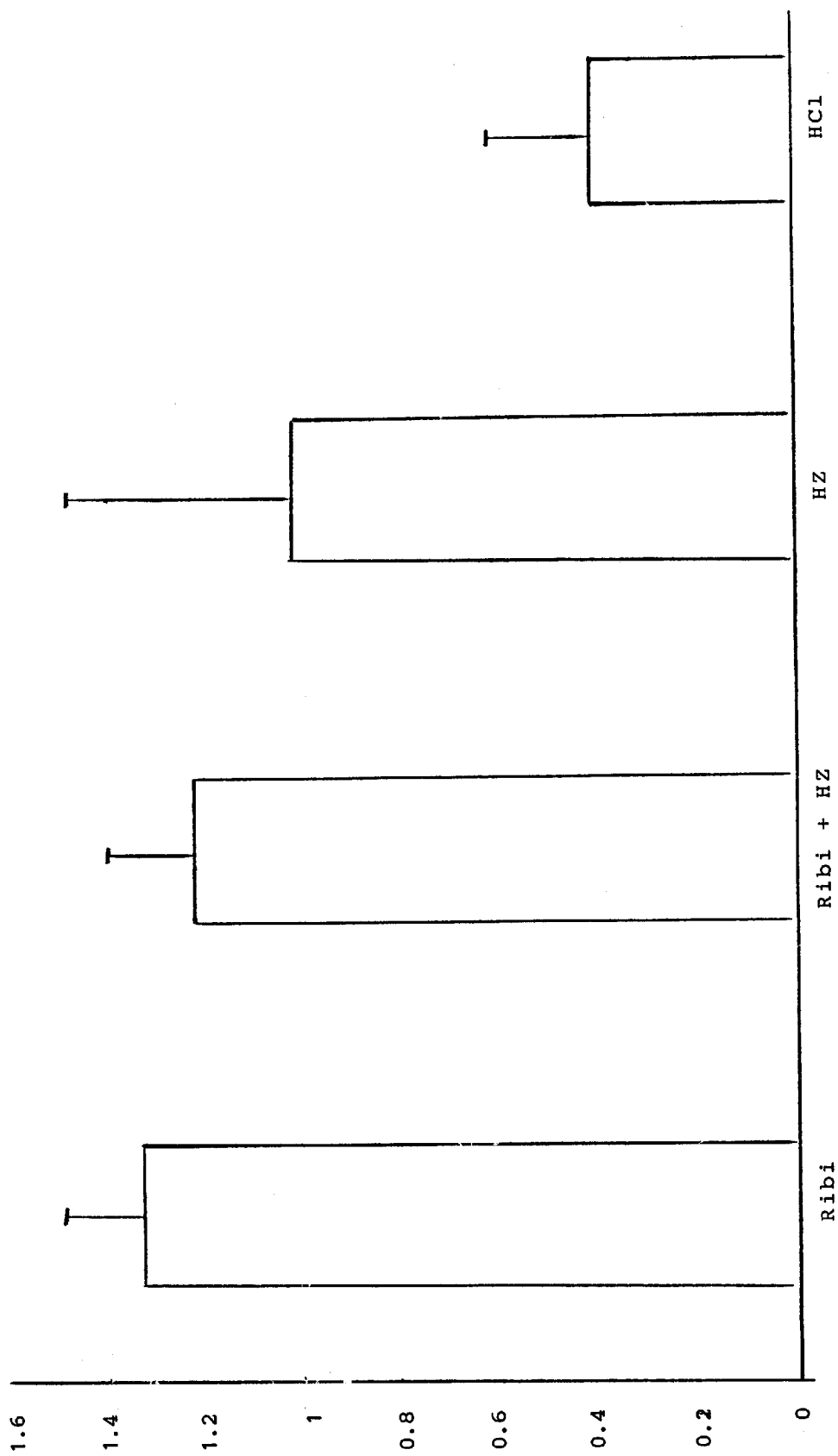
FIG. 1 illustrates an in vivo experiment comparing vaccine adjuvants as between the inventive hemozoin adjuvant and a commercially available lipid-A vaccine adjuvant (Ribi Adjuvant System (R-700) Ribi ImmunoChem Research Inc. Hamilton Mont.) with the antigen RNase. The figure compares serum antibody titers of anti-RNase IgG antibodies for mice immunized with the RNase antigen plus the lipid-A adjuvant ("Ribi alone"), the lipid A adjuvant plus the inventive hemozoin adjuvant ("Ribi+HZ"), the inventive hemozoin adjuvant ("Hz alone"), or control hemin chloride ("HCl"). These data show the equivalence in immunogenicity as between the lipid A adjuvant and the hemozoin adjuvant and the lack of any additive or synergistic effect of the combination of both adjuvants.

The present invention provides an adjuvant composition for potentiating the immunogenicity of an antigen, comprising (a) water or an aqueous solution; and (b) hemozoin or β-hematin.

Digestion of host erythrocyte hemoglobin by malarial parasites (e.g., *Plasmodium falciparum*) results in release of heme. The heme is rendered non-toxic by polymerization to an insoluble polymer called hemozoin. Hemozoin was first noted as dark brown discoloration of the liver, spleen and brain in patients who died from a malaria infection. Proteolysis of hemoglobin releases heme, which when soluble is highly toxic to biological membranes. Malarial parasites lack heme oxygenase and are, therefore, unable to cleave heme into an open-chain tetrapyrrole. Thus, heme is not excreted from the parasite cells but is, instead, converted to hemozoin by a process unique to the malarial organism. Hemozoin is released along with merozoites when infected erythrocytes burst and this is scavenged by macrophages.

Hemozoin has been purified from malaria parasites by a process described in Slater et al., *Proc. Natl. Acad. Sci. USA* 88:325–329, 1991. Briefly, a crude extract of hemozoin (Yamada and Sherman, *Exp. Parasitol.* 48:61–74, 1979) was obtained for purification. A crude hemozoin extract can be prepared, for example, from cultures of human erythiocytes infected with *P. falciparum* synchronized at the late trophozoite stage. The UV/visible absorbance spectrum of an aqueous suspension of the purified material was similar to that of hemozoin in a crude parasite extract. Hemozoin has an absorbance peak between 650 and 652 nm.

The crude, purified hemozoin preparation was suspended in a carbonate/bicarbonate buffer by brief sonication and removed from solubilized contaminants by brief centrifuigation at 25,000×g for 30 min at 4° C. In order to solubilize any contamination membranes, crude hemozoin was extracted twice for three hours in buffer (50 mM Tris HCl, pH 7.4) containing 0.2% (by weight) sodium dodecyl sulfate at room temperature. After centrifugation, a hemozoin pellet was washed three times in bicarbonate buffer and residual proteins were removed by an overnight digestion in buffer containing proteinase E at 1 mg/ml. The insoluble material was recovered and washed as described herein and then extracted in 6M urea for 3 hr at 4° C. The purified hemozoin can be used directly in an aqueous form to produce the adjuvant or it can be stored in a dried form. To dry the purified hemozoin preparation, the material was pelleted by centrifugation, washed with distilled water, lyophilized and then further dried over $P_2O_5$.

It is also possible to prepare a "hemozoin" synthetically from hemin chloride. The synthetically-prepared hemozoin has been called β-hematin. A procedure for synthesizing β-hematin has been described in Slater at al., *Proc. Natl. Acad. Sci. USA* 88:325–329, 1991. Briefly, 60 μmol of hematin (Aldrich) were dissolved in 8 ml of 0.1M NaOH. The porphyrin was precipitated by the addition of 49 mmol of acetic acid, and the resulting suspension heated overnight at 70° C. The precipitate was extracted three times with 0.1M bicarbonate (pH 9.1), washed four times in distilled water, followed by two times in 100% ethanol, and finally resuspended in serum-free RPMI medium to final concentrations ranging between 1.0 and 1.5 nmol heme per ml. This material (β-hematin) was determined to be chemically identical to purified native hemozoin as assessed by infrared and x-ray absorption spectroscopic analysis.

Dried hemozoin is prepared into an adjuvant form by suspending the hemozoin is an appropriate aqueous adjuvant vehicle, such as saline or buffered saline. Alternatively, an aqueous solution of hemozoin or β-hematin can be suspended and sonicated to improve the suspension properties of the aqueous hemozoin of aqueous β-hematin preparation. In addition, there are other agents that can help form an emulsion within an adjuvant formulation to better suspend the hemozoin in the adjuvant. For example, water soluble polymers, such as polymers of acrylic acid cross linked with polyallyl sucrose (commercially available under the name of Carbopol). Approximately equal amounts of acrylic acid cross linked with polyallyl sucrose with hemozoin should be formulated according the U.S. Pat. No. 5,026,546, the disclosure of which is incorporated by reference herein.

Another formulation will avoid the last lyophilization and drying steps when preparing hemozoin and instead suspend the hemozoin in an aqueous formulation (e.g., saline or buffered saline) and sonicate the formulation to suspend the hemozoin in aqueous solution. One must shake the suspension thoroughly before each use.

Preferably, the adjuvant composition further comprises a lipid of fat emulsion comprising about 10% (by weight) vegetable oil and about 1–2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

The present invention further provides a method for inducing or enhancing the immunogenicity of an antigen in a mammal, comprising parenteral administration of a pharmaceutical composition comprising the antigen and an effective amount of hemozoin. Preferably, the lipid or fat emulsion comprises about 10% soybean oil and about 1.2% egg yolk phospholipids. Preferably, the antigen is selected from the group consisting of a vaccine, bacteria, virus, rickettsia, pollen, dust, danders, a poison, and venom derived from an insect or snake.

The present invention further provides a method for using hemozoin as a vaccine adjuvant.

EXAMPLE 1

This example illustrates the experiment shown in FIG. 1 providing in vivo data supporting hemozoin or β-hematin as an adjuvant. BALB/c mice were divided into four groups of five mice each. The schedule was to first bleed the mice to determine background antibody levels of IgG to RNase antibody on day -2. Immunizing began on day 0, there was an antibody titer determination on day 10 and the mice were "boosted" with another immunization of day 13. Another antibody titer determination was made on day 23. Antibody levels were determined by ELISA (enzyme-linked immunosorbent assay). Briefly, Immunulon II plates (Dynatech, Chantilly, Va.) were coated with Rnase (50 ng/well in sodium bicarbonate buffer, pH 9.5) and blocked with Superblock (Pierce, Rockford, Ill.). Mouse serum, diluted 1:200 in TBS (20 mM Tris pH 7.4, 150 mM NaCl) containing 0.2% Tween 20, was added and incubated for 2 hours at room temperature. The plates were washed five times with TBS containing 0.2% Tween 20. Specific anti-RNase antibodies were revealed following incubation with goat-antimouse IgG conjugated to horseradish peroxidase (Boehinger Manheim, Indianapolis, Ind.). The substrate was OPD and the plates were read at 490 nm. The data presented is the antibody titers taken after the second immunization on day 23.

Antigen ribonuclease A (RNase) from bovine pancreas was obtained commercially from Sigma. Each mouse was injected with 50 μg of antigen in 100 μl of antigen solution (500 μg/ml) diluted with 100 μl of adjuvant solution. The adjuvants were (1) a commercial Lipid A adjuvant (Ribi Immunochem Research, Hamilton, Mont.) containing 1 mg Lipid A in an emulsion of 2% oil Tween reconstituted to 2.0 ml.; (2) the Ribi adjuvant of #1 plus a hemozoin adjuvant (0.3 µMoles/mouse) made from synthetic β-hematin by the process described herein; (3) hemozoin adjuvant (0.3 µMoles/mouse) again made from synthetic β-hematin by the process described herein; and control hemin chloride monomer (0.3 µMoles/mouse).

The results are shown in FIG. 1 and illustrate that the hemozoin (β-hematin) adjuvant was as effective as the known adjuvant Lipid A but not additive with Lipid A.

We claim:

1. An adjuvant composition for potentiating the immunogenicity of an antigen, comprising a suspension of
   (a) water or an aqueous solution; and
   (b) hemozoin or β-hematin.

2. The adjuvant composition of claim 1, further comprising a lipid or fat emulsion comprising about 10% (by weight) vegetable oil and about 1–2% (by weight) phospholipids.

3. The adjuvant composition of claim 1, further optionally comprising an emulsion form having oily particles dispersed in a continuous aqueous phase, wherein the emulsion form consists essentially of an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

4. A method for inducing or enhancing immunogenicity of an antigen in a mammal, comprising parenterally administering of a pharmaceutical composition comprising the antigen and an effective amount of hemozoin or β-hematin.

5. The method of claim 4, wherein the pharmaceutical composition further comprises a lipid or fat emulsion having about 10% vegetable oil and about 1–2% phospholipids.

6. The method of claim 4 wherein the antigen is selected from the group consisting of a vaccine, bacteria, virus, rickettsia, pollen, dust, danders, a poison, and venom derived from an insect or snake.

7. A method for administering a vaccine, comprising adding hemozoin or β-hematin as a vaccine adjuvant.

8. The method of claim 5 wherein the vegetable oil is soybean oil and the phospholipid is from egg yolks.

* * * * *